United States Patent
Weber et al.

(10) Patent No.: US 6,638,238 B1
(45) Date of Patent: Oct. 28, 2003

(54) LIPOSUCTION CANNULA DEVICE AND METHOD

(75) Inventors: Paul J. Weber, Ft. Lauderdale, FL (US); Steven R. Visuri, Livermore, CA (US); Matthew J. Everett, Livermore, CA (US); Luiz B. Da Silva, Pleasanton, CA (US); Alwin H. Kolster, Anaheim, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/458,134

(22) Filed: Dec. 9, 1999

(51) Int. Cl.[7] .................... A61B 17/20; A61B 17/32
(52) U.S. Cl. .................... 604/22; 604/902; 606/171
(58) Field of Search .................... 604/22, 902, 19, 604/20, 21, 43; 607/97; 606/159, 167, 170–172, 180

(56) References Cited

U.S. PATENT DOCUMENTS

| | | | | |
|---|---|---|---|---|
| 4,932,935 A | * | 6/1990 | Swartz | 604/22 |
| 5,695,507 A | * | 12/1997 | Auth et al. | 606/159 |
| 5,941,825 A | * | 8/1999 | Lang et al. | 600/449 |
| 6,007,513 A | * | 12/1999 | Anis et al. | 604/22 |
| 6,287,271 B1 | * | 9/2001 | Dubrul et al. | 604/22 |
| 6,436,116 B1 | * | 8/2002 | Spitz et al. | 606/170 |

* cited by examiner

*Primary Examiner*—Sharon Kennedy
(74) *Attorney, Agent, or Firm*—Michael C. Staggs; Alan H. Thompson

(57) ABSTRACT

A liposuction apparatus and method optionally having a sonic or ultrasonic source with an axial lumen passage in which the shaft can be made to reciprocate (oscillate) in a non-rectilinear fashion. The apparatus may also contain the concomitant use of rectilinear reciprocation motion in addition to ultrasonic motion or energy along the shaft of the apparatus. The advantages of the liposuction apparatus are as follows: 1) non-rectilinear single shaft reciprocating cannula, 2) sonic or ultrasonic energy delivered to the distal tip, 3) rectilinear reciprocating cannula with ultrasonic energy along the shaft from the handle, and 4) any of the above reciprocating components powered by excess unused vacuum capacity in the liposuction aspirator (suction engine) apparatus. There are three (3) primary sources of energy applied to the cannula shaft: the first is the oscillating surgeon's arm motion (approximately 1–2 hertz); the reciprocating motion (of about 100 Hz); and the optional concomitant motion as delivered by the ultrasonic energy (e.g. 25 KHz).

24 Claims, 5 Drawing Sheets

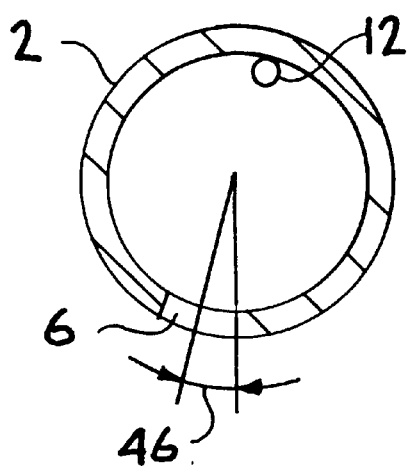
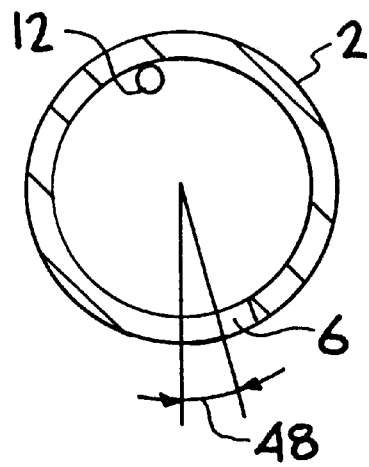
FIG. 6A    FIG. 6B
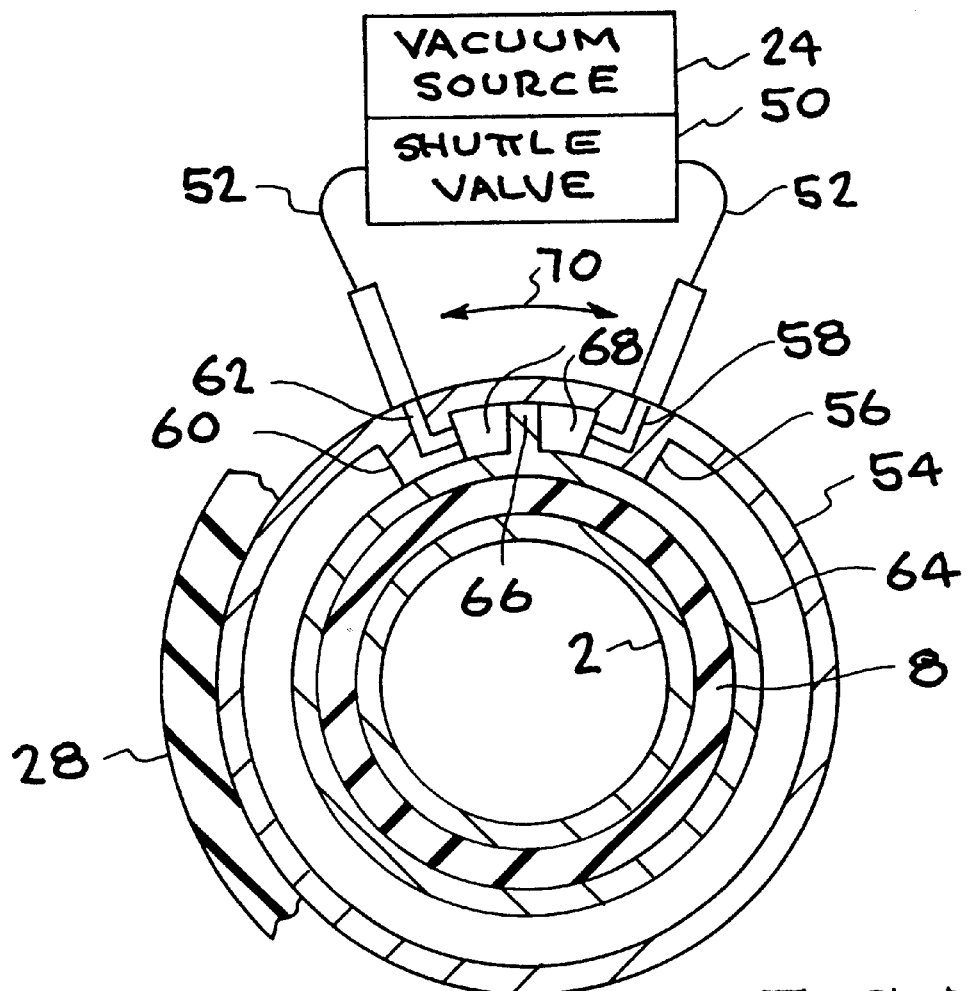
FIG. 7

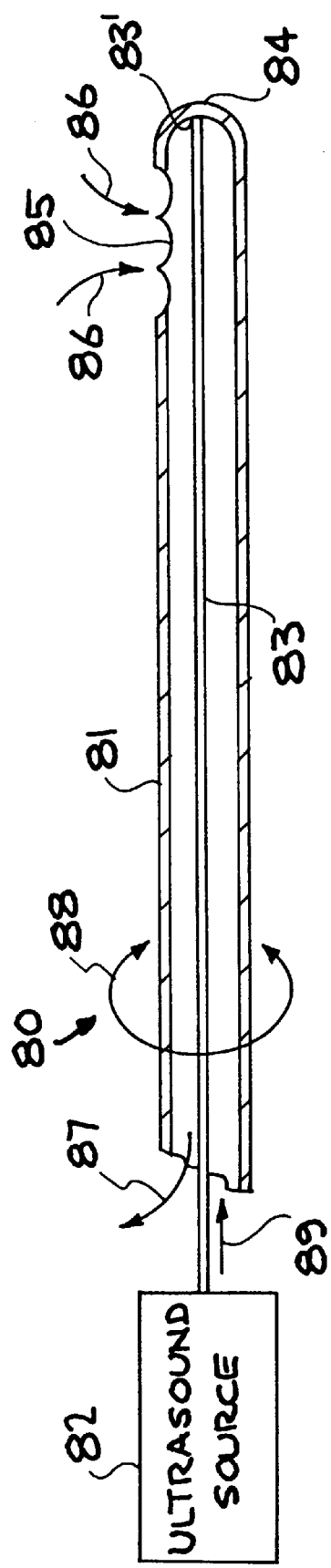
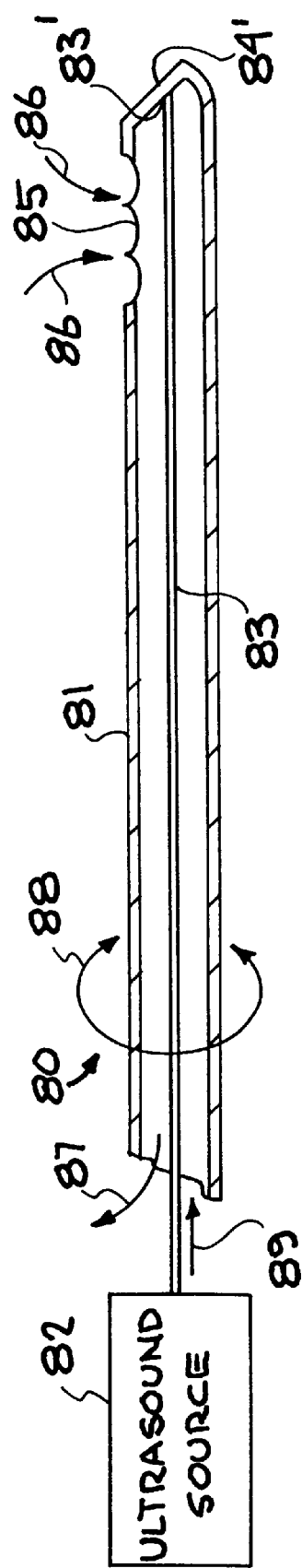
FIG. 8A
FIG. 8B

LIPOSUCTION CANNULA DEVICE AND METHOD

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates to a liposuction apparatus and method. More particularly, this invention relates to a liposuction apparatus optionally having a sonic or ultrasonic source with an axial lumen passage in which the shaft can be made to reciprocate in a non-rectilinear fashion. The apparatus and method may also contain the concomitant use of rectilinear reciprocation motion in addition to ultrasonic motion or energy along the shaft of said device.

2. Description of the Prior Art

Liposuction, which literally means "fat suction", is a technique to remove intact fat cells, fat globules, fatty fluids or fatty debris from the body by means of teasing, pulling, scraping, sonication, suction and/or pressing out the debris. Liposuction can be used to reduce the volume of fat in many regions of the body, but liposuction is particularly effective in such areas as the thighs and the abdomen where fat is less responsive to diet and exercise. Liposuction, performed as an elective operation, is one of the most common surgeries performed in the world.

There are now several main forms of liposuction used by surgeons to extract fat. Each of these modalities varies in its necessity or usefulness, depending upon the area of the body being treated, the amount of fibrous tissue which is mixed in with the fat to be treated, the number of times the fat has been previously suctioned (which usually increases the fibrous and resistant nature of the fat), and the genetic makeup of the individual patient (African-American and Mediterranean ancestry patients and males usually have more fibrous fat). Herein follow some of the condensed benefits and more expanded upon drawbacks of each modality so as to differentiate our proposed devices from the prior art.

In traditional liposuction, a single lumen cannula shaft, attached to a handle, is pushed by a surgeon through skin entrance sites into the target fat in a spoke-wheel or radial fashion. Unfortunately, chronic and acute stress on the surgeon's elbow and shoulder can fatigue the surgeon, thus reducing the reproducibility of the result between the patient's right and left sides, and sometimes making for a less than optimal result. When a liposuction cannula passes through the target tissue, it tends to suck out or traumatize a diameter of fat that is related to the diameter of the shaft of the cannula. Ideally, one would use the smallest diameter shaft possible to reduce penetration injuries. Unfortunately, liposuction would take excessive time to perform with ultra-small (less than 2 mm) cannulas. Some surgeons utilize small cannulas that vary on the size of syringe needles. This work takes numerous hours to perform and is impractical for the average surgeon with typical time and anesthetic constraints. Additionally, the performance of numerus liposuction procedures and the necessity to move the surgeon's arm back and forth so many times within a unit period of time has led to surgeons having physical conditions similar to tennis elbow and arthritis of the involved joints. Most surgeons thus use larger single lumen cannula shafts, up to 4 to 6 mm in diameter. Unfortunately, these larger diameter cannulas often leave noticeably large waves behind in the patient's target fat area and surface skin resulting in an unpleasant, non-uniform appearance to the skin.

In a review by Weber et al, Reinforced Swan-Neck, Flexible Shaft, Beveled Liposuction Cannulas (The American Journal of Cosmetic Surgery) 16(1): 41–47, 1999, dynamics of liposuction cannula tips were discussed. Although smaller tips and shaft diameters require less energy from the surgeon to penetrate fibrous fat, less fat per unit time is removed. Larger diameter cannulas remove fat faster, but require greater effort and tissue trauma. It is difficult to find a happy medium, although sometimes the choice of a cannula tip can reduce the exertion necessary to pass through fibrous fat. (See above referenced Weber et al, American Journal of Cosmetic Surgery.)

Ultrasonic liposuction cannulas were developed by Parisi et al in the late 1980's and patented under the patents "Liposuction Procedure With Ultrasonic Probe", U.S. Pat No. 4,886,791 and "Ultrasonic Probe", U.S. Pat. No. 4,861,332 (1988). Parisi claims that the ultrasonic process "melts" fat. Only if the word "melt" is used extremely loosely and re-defined is this true. Fat stored in the body may be encapsulated in cells and is not truly solid to any degree. The ultrasonic cannula uses water as a coupling medium in order to break apart fat cells and fat globules, thus releasing fat from the aforementioned cells and fibrous tissues which provide support and structure to the human fat. Parisi saw early on that the tremendous heat generated by the ultrasonic liposuction cannula could be detrimental to the patient and therefore requires significant cooling measures. The material which follows will demonstrate three generations of ultrasonic liposuction cannulas based upon the Parisi patents, which still do not provide an adequate solution.

Three (3) Generations of Ultrasonic Liposuction

The newest (third generation) ultrasonic liposuction cannula is basically cooled along the length of the cannula shaft by an outer metal sleeve that almost covers the vibrating tip. Sterile cooling water passes between the hot inner vibrating shaft and the outer metal sleeve. The cooling water exits at the tip of the cannula as a "bubble" of water. Disadvantageously, the metal cooling sleeve leaves only a fraction of an inch of vibrating shaft (tip) exposed to the patient's tissue. This design change is alleged to reduce the tendency for thermal burns. A major drawback for the third generation of ultrasonic cannulas is that there is incomplete suction of the sonicated (broken and foamy) fat out of the patient's tissues. The broken down fat remaining in the patient must be crudely pressed out with rollers, suctioned out with old-fashioned cannulas or left to be "absorbed" inside the patient's body. The long term effects of leaving foamy fat and broken down fat cells behind in the body have not been determined. For example, degraded fat may cause more fibrosis of the treated areas, or the liver or vessels may be damaged by fatty infiltration due to overload.

The third generation still suffers the possibility of causing thermal burns wherein a hot cannula tip strikes or harms the skin. Another problem with ultrasonic liposuction is that the tip can become extremely hot when impacting a dense bodily structure if the ultrasonic cannula is moving too slowly.

Some of the disadvantages of ultrasonic liposuction, no matter what generation of cannula is used, are currently unknown to many patients. Ineffectively, surgeons use rolling pins to "squish out" the remainder of the liquefied fat out of the patients. This means that the current ultrasonic cannulas are suction-inefficient, perhaps leaving up to one-half of the sonicated fat behind. Current cannulas do not have holes large enough or exposed enough to completely suction-up the fat that is sonicated and liquefied. Fatty acids are a known source of inflammation in the human body and may cause the body to lay down scar tissue and other unwanted reactions. Additionally, the tunnels and unsonicated liquefied oils and their by-products likely contribute to the formation of seromas (fluid ball collections) so commonly seen with ultrasonic liposuction procedures. Using rollers is not an optimal way to remove fat and is only partially successful. Current ultrasonic liposuction cannulas cannot bend sufficiently and still vibrate (sonicate) the desired target structures. Early generations of ultrasonic liposuction cannulas, which are still currently in use in many offices throughout the United States, incorporate large "protectors" that are screwed into the patient's skin to protect the entrance sites from burns. These "protectors" make for even larger scars at the entrance wounds. Another disadvantage of the third generation liposuction cannula is that the cooling sleeve portion adds 2 mm to the diameter of the cannula. The current long-shaft version of the third generation ultrasonic liposuction cannula has a diameter of over 6 mm. Larger entrance sites (wounds) cause larger scars following the procedure. Ultrasonic liposuction is most helpful in areas of the body that are very thick and fibrous, e.g., areas where liposuction is being done for a second or more time, the back region, and the male breast region where the fat can be thick and heavily coursed by fibrous tissue.

Some surgeons feel that they produce safer and less burning results with the latest ultrasonic cannulas when the cannula setting is reduced to 50 per cent maximum energy. Unfortunately, this 50 per cent ultrasonic energy reduction results in a more difficult passage of the cannula through fibrous fat. It would, therefore, be highly desirable to be able to reduce the ultrasonic energy necessary to penetrate the fibrous or target fat by the addition or combination of another energy source within the liposuction cannula shaft.

There are three primary sources of energy that may be applied to the cannula shaft. The slowest of motions is the oscillating surgeon's arm motion, approximately one to two hertz. Intermediate 100 hertz motion is provided by reciprocating action (see below). Motion at 25,000 hertz may be delivered via ultrasonic energy.

In an effort to reduce the energy required for the surgeon's arm to bore through fibrous fat, in the late 1980's a 100 hertz rectilinear motion induced by motors was proposed for the cannula handle. Some of the early prototypes for rectilinear motion were manufactured (well prior to patents being issued) for individuals by KMI (Kolster Medical Inc.) in Los Angeles, Calif. Discussions with Mr. Kolster revealed that in the late 1980's KMI was already manufacturing reciprocating rectilinear liposuction cannulas. The frequency of oscillation of the shafts was roughly 100 hertz. In the past there were difficulties with cost and sterilization considerations, as well as durability following numerous sterilizations. Since the late 1980's there have been several patents granted for various reciprocating liposuction cannula devices.

Although the reciprocating devices which have been previously patented and/or are in clinical use do cause rubbing, abrasion, shearing or tearing of the fat globules as they fall into the reciprocating cannula tip, it is possible that the true principal dynamic involved in the use of a reciprocating device is to expose a greater amount of cannula tip port to the external fat to be suctioned. For example, if a 2 mm wide by 10 mm long cannula fat entrance port were to oscillate on an arc 2 mm to the right and 2 mm to the left, the effective surface area (size) of the port would be tripled. Additionally, if a 2 mm wide by 10 mm long cannula entrance port were reciprocating in a to and fro direction and it reciprocated 5 mm forward and 5 mm backward, this would only double the effective zone in which fat (or aspirate) could be entrapped.

It has been shown that additional but relatively small amounts of ultrasonic energy can loosen target fat sufficiently and enhance the procedure.

The prior efforts rely upon the process of slicing or cutting in which two shafts, both an inner and an outer shaft, move in dissimilar directions, align windows for an instant (allowing a window or port of availability for the fat to fall into at the very distal tip and be sliced off), followed by alleged "cutting" as the two shafts and windows move again in different directions. Any surgeon who has performed a sufficient number of liposuctions will be able to verify that the fibrous sepral bands which course through the fat nourish it and provide support, and are of a very strong nature similar to the tough white bands found in steaks that are uncooked. It is highly improbable that any of the prior art just described would succeed in operating for sufficient time to complete a typical procedure without becoming completely clogged with fibrous tissue or having fibrous tissue catch in between the dissimilarly moving shafts, thus ceasing operation of the proposed devices. These devices in non-disposable form would likely be impractical for common usage in liposuction, especially in large areas in which the target fat is fibrous in nature. Fibrous target fat exists in one of every two patients.

Further embodiments of the prior art include motors for the reciprocation which are powered by electricity and/or gas. Close inspection of the prior art reveals that none of the gas-powered instruments utilize the available excess vacuum power that is present currently in all offices that are performing liposuction. Since the late 1980's the vacuum-powered suction machines have become exceedingly strong, capable of delivering vacuums of −40 torr. The non-electrical prior art basically relies upon gas-powered mechanisms that provide a positive pressure in order to generate the energy by which a reciprocating mechanism can be driven. Motors or pressurized gas cannisters cost money in that the positive pressure fluid source must be used to generate the power. Additionally, mechanization must be present within the liposuction cannula to utilize the positive pressure power. Additionally, extra hoses must come into the liposuction cannula, thus causing a tangled hose mess for the surgeon who is already having to keep up with two additional hoses (if ultrasonic suction is performed with a water cooling hose and an electrical control line), which is in addition to the suction line.

The liposuction device and method of the present invention is dissimilar to the prior art apparatus in that in this invention the cannula shaft does not require two separately moving shafts in order to catch fat between two aligned "windows" or to cut and remove fat. Also, the present invention differs from the prior art in that only a single shaft is necessary to effect the removal of the target fat. A second shaft or additional lumen is also in the present invention but its design, function and purpose is for the novel combination of cooling the tip of the hot vibration ultrasonic device, and optionally to equilibrate the pressure or provide additional pressure in order to allow fat to move back up the cannula shaft with greater ease as opposed to traditional and previous ultrasonic liposuction cannula shafts. The liposuction device of this invention involves a novel combination of the uses of reciprocating energy (e.g. at 100 Hz) plus ultrasonic energy (e.g. at 25 KHz) in which the dual use of both energies would reduce the total energy of each specific type, i.e., reduced ultrasonic energy and reduced reciprocating energy to be used. In addition, the device of this invention may uniquely use suction (vacuum/negative pressure) to cause a desired and controllable reciprocating motion of the liposuction shaft. For example, vacuum pump capability approaches −40 torr, but optimally only mild negative pressure in the range of −10 to −15 torr is used for suctioning in order to reduce trauma to the fatty tissues. Excess vacuum capacity may be utilized to generate reciprocating motion within the cannula shaft.

SUMMARY OF THE INVENTION

It is an object of the present invention to provide an improved reciprocating liposuction cannula apparatus and method.

A further object of the invention is to provide an axial (rotational) reciprocating liposuction cannula apparatus which utilizes a single moving shaft for slicing or cutting.

Another object of the invention is to provide a liposuction apparatus and method which utilizes a combination of reciprocating energy (rectilinear or axial) and ultrasonic energy in which the dual use reduces the total energy of each type necessary to complete a "given" liposuction surgery.

Another object of the invention is to provide a liposuction apparatus and method which utilizes excess available negative pressure (vacuum) capacity for controllable reciprocating motion of the liposuction cannula shaft.

Another object of the invention is to provide a reciprocating liposuction cannula apparatus which uses a non-rectilinear single shaft action reciprocating cannula.

Another object of the invention is to provide a liposuction cannula apparatus which utilizes a rotational oscillation motion.

Another object of the invention is to provide a liposuction cannula apparatus and method which can be operated in a non-rectilinear reciprocating action or in a rectilinear reciprocating action in combination with ultrasonic energy.

Other objects and advantages of the present invention will become apparent from the following description and accompanying drawings. This invention involves a liposuction cannula apparatus and method which utilizes a single reciprocating shaft that preferably operates in a rotational oscillation action. The apparatus optionally has a sonic or ultrasonic source with an axial lumen passage in which the shaft can be made to reciprocate in a non-rectilinear fashion. The apparatus may also contain the concomitant use of rectilinear reciprocation motion in addition to ultrasonic motion or energy along the shaft of the apparatus. The apparatus of the invention utilizes a combination of reciprocating energy and ultrasonic energy. Also, the apparatus utilizes available excess vacuum (negative pressure) power for controllable reciprocating motion. In addition, the apparatus uses an internally located tube for cooling and pressure equilibration, which is the exact opposite of the prior art.

BRIEF DESCRIPTION OF THE DRAWINGS

The accompanying drawings, which are incorporated into and form a part of the disclosure, illustrate embodiments of the invention and together with the description serve to explain the principles of the invention.

FIG. 6A and FIG. 6B are cross-sectional views near the distal cannula tip.

FIG. 7 is a cross-section/schematic of an alternate method for obtaining the oscillating motion.

FIG. 8A is a partial view of a cannula shaft with an ultrasound source mounted thereto.

FIG. 8B illustrates a beveled distal end of the shaft of FIG. 8A.

DETAILED DESCRIPTION OF THE INVENTION

Figure 1:
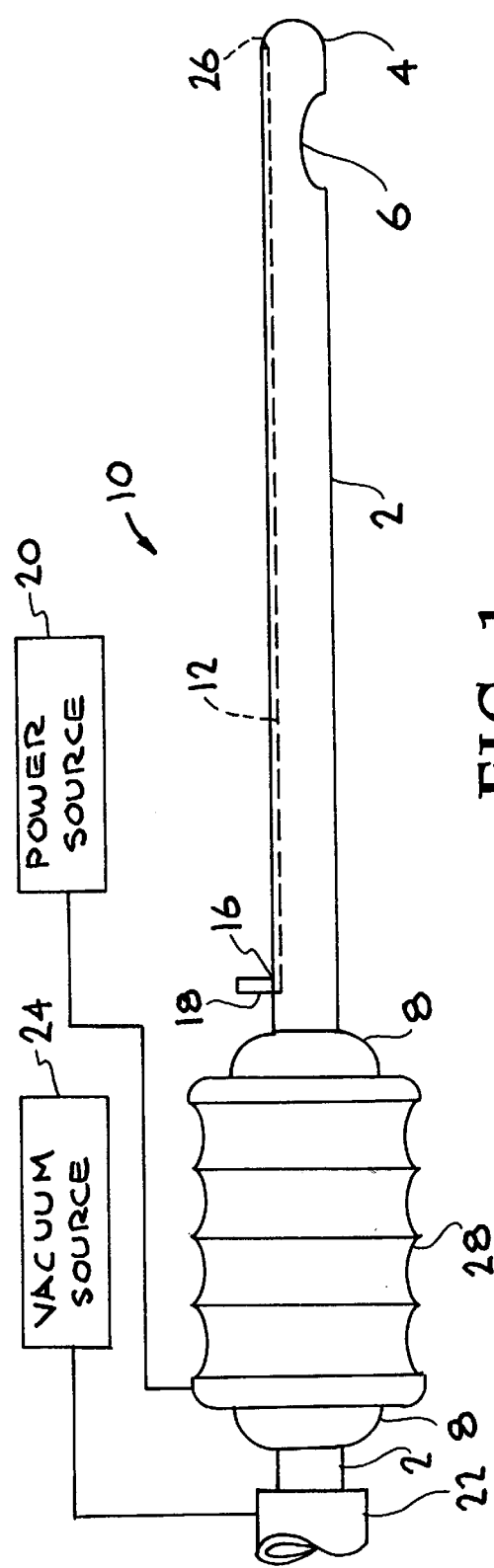
FIG. 1 is an overall view of an embodiment of a liposuction cannula device made in accordance with the present invention.

The present invention is directed to a reciprocating liposuction cannula apparatus or device which utilizes a single cutting shaft, may utilize a combination of reciprocating energy and ultrasonic energy, and may utilize available excess (over that required for suction) vacuum (negative pressure) capacity to produce the reciprocation of the cannula shaft. One embodiment of this invention uses a single shaft for cutting, preferably in a non-rectilinear oscillation motion. An additional lumen may be utilized for cooling of the cannula tip, equilibrating the pressure, or providing additional pressure to allow fat to move back up the cannula shaft with greater ease. The combination of reciprocating energy and ultrasonic energy reduces the total energy of each type. Also, in this non-rectilinear reciprocating form of the cannula device, no protective measures (monitoring tip impact) need be taken in order to prevent the device from battering through important organs.

The combination of ultrasonic and reciprocation energy reduces the amount of ultrasonic energy necessary to deliver a given effect on the tissue. Thus, less ultrasonic trauma will affect the target tissues. Since less ultrasonic energy will be needed to sonicate the tissues, the cooling sleeve can be made of teflon, plastic or metal and receded from the tip of the vibrating liposuction cannula. Also, a lumen contained within the shaft of the cannula can provide internal end cooling to the tip, reducing the need for a protective fluid cooling sleeve on the outside of the device. As an example, a low flow rate of sterile water could be pumped through the inner lumen to the distal cannula tip to efficiently cool the cannula.

In a non-rectilinear reciprocating device, the oscillating nature of the tip and attached shaft will allow for a greater "visibility" of the cannula entrance port to target fat. The suction hole (fat entrance port) located at the distal tip may "see" and thus suction more fat, which will thus deposit and slide down the cannula shaft and be suctioned out of the patient. This device also involves the use of scalloped edges that will not tear blood vessels as the device passes through living tissue and fat. Trauma and bleeding to outlying tissues should be minimized since fat via the fibrous supporting septae are nourished by blood vessels that pass in the thin fibrous elements. The device of this invention would reduce the arm motion of the surgeon necessary to remove the fat, thus reducing the elbow and arm problems discussed above. The combination of any reciprocating plus ultrasonic liposuction will reduce the necessary ultrasonic energy needed to penetrate fibrous fat and will still provide an overall reduction in the effort necessary to remove fibrous fat by the surgeon. The effective diameters of liposuction cannulas of this invention may range from 2–6 mm.

The invention involves the use of the suction (vacuum/negative pressure) energy to cause a desired and controllable reciprocating motion of the liposuction cannula shaft, as pointed out above. The vacuum-driven reciprocating motion is optimally suited to the non-rectilinear action in that rotational oscillation twisting reduces the need for a mechanism for reciprocation interruption as this particular embodiment does not batter forward the tissues that are being treated. In addition, rotational oscillation motion does not require the larger amounts of energy that would be necessary to linearly force a cannula through fibrous fat. Rotational oscillation motion alone or in combination with ultrasonic energy will not be stopped by encountering fibrous fat to any large degree as would a rectilinear operated reciprocating device. The efficient use of flaps and valves will enable the excess available suction that is used to suction the fat from the human body to be used to create the reciprocating motion within the cannula shaft. It is noted that full use of a suction motor capability (approaching –40 torr) literally tears fat from the human body and causes more bleeding and problems such as edema (trauma swelling) following surgery. It is recommended by most manufacturers that current liposuction cannulas be used with a vacuum (negative pressure) in the range of –10 to –15 torr in order to reduce trauma to the fatty tissues and their surrounding tissues. There is a lot of excess capacity in the form of a vacuum that can be generated by the liposuction vacuum machine (aspirator) between –10 to –15 torr to –40 torr. This extra available vacuum power is utilized in the side-to-side action to generate rotational oscillating motion within the cannula shaft.

A small filter can be placed upon the source of the equilibrating gas that will pass through the suction tubing, if desired. However, it is noted that virtually all surgical rooms have air sterilization equipment and other ionic means for reducing bacteria in the air so that contamination and infection are not a concern. For example, currently when the surgeon removes the traditional liposuction cannula from the patient's body, room air is allowed to pass through the shaft. Thus, there is no concern for contamination using this method as it is actually similar to common currently used techniques.

Beveled cannula shaft tips and other configured tips can be used in the device of this invention. Temperature control and sensors can be used throughout the device in order to maintain a computer monitored uniform temperature.

Referring now to the drawings, various embodiments of the reciprocating liposuction device made in accordance with the present invention are illustrated.

FIG. 1 shows an overall view of the liposuction cannula of the present invention. The device 10 consists of essentially two main parts. The cannula tube body 2 and the handle/motor unit 28, can be seen in cross-section in FIG. 3. The cannula tube body 2 has a rounded (or optionally beveled) tip 4 with a port (opening) 6 adjacent to tip 4. The tip 4 may be beveled as seen in FIG. 8B. Internal to the tube body 2 is the pressure relief tube 12, shown as a dotted line. The pressure relief tube 12 has an open end 26 near the tube body tip 4. The pressure relief tube 12 exits the tube body 2 at a point 16 near the handle/motor unit 28 and is connected to a tube 18. The handle/motor unit 28 is connected to a power source 20. The tube body 2 is connected by tube 22 to said vacuum or negative pressure source 24. The device 10 is assembled by inserting tube body 2 in the handle/motor unit 28 and connecting the tubes 18 and 22 at the appropriate positions. The flexible grippers 8 make contact with the outer diameter of tube body 2 and transmit the torque from handle/motor unit 28 to provide the required reciprocal motion.

Figure 2:
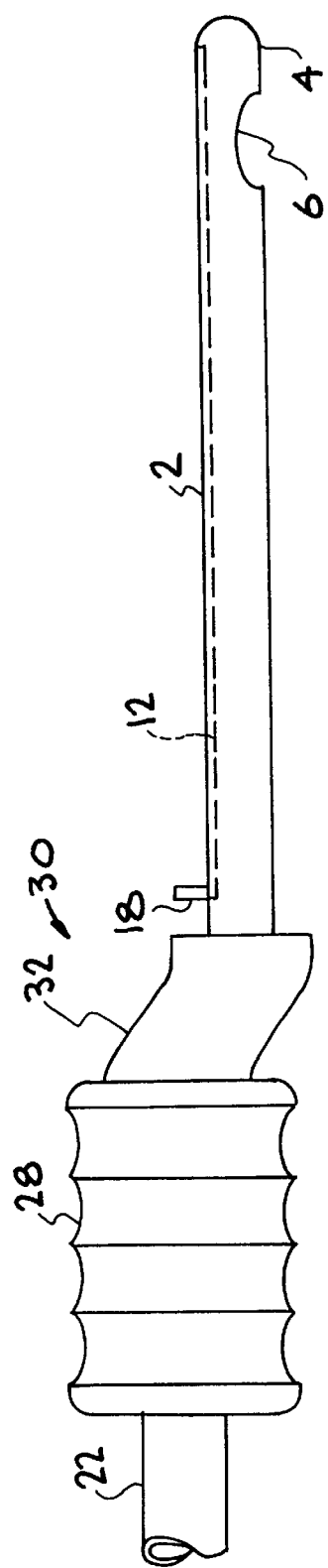
FIG. 2 is an overall view of an alternate design for the liposuction cannula device.

FIG. 2 shows an alternate method of applying the motion generated by handle/motor unit 28 to the tube body 2. In this embodiment the gripper means 32 is an elongated flexible member that can assume different positions such as the one shown in FIG. 2 which we shall describe as being a "swan's neck" wherein the axis of the shaft is offset from the axis of the handle. In this device, indicated at 30, the tube body does not pass through the handle/motor unit 28 but terminates within the elongated gripper 32. The connection to tube 22 is also within gripper 32 and does pass through the handle/motor unit 28 and then connects to vacuum source 24, as did device 10. The tube body 2 is similar to the tube body of device 10 in that it has a tip 4, port 6, and an internal pressure relief tube 12 connected to tube 18. The same tube 2 used in device 10 can be used in device 30 resulting in a slightly longer overall length for the device.

Figure 3:
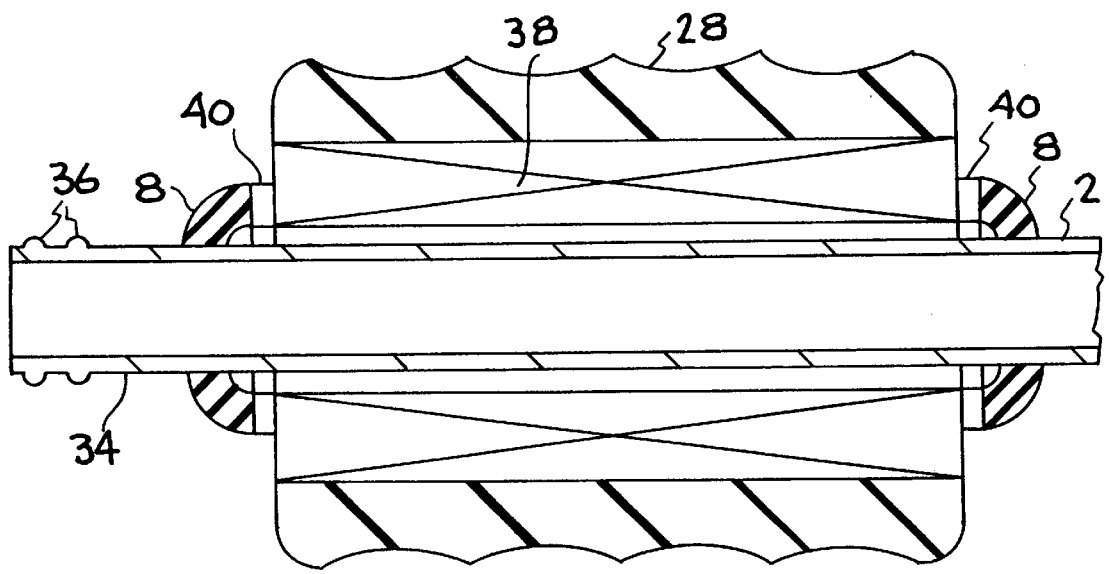
FIG. 3 is a cross-section of the handle end of the liposuction device.

FIG. 3 shows a cross-section of the handle motor unit 2 of device 10. The handle of handle/motor unit 28 is part of the outer housing of motor 38. Moving parts 40 of motor 38 are joined to flexible grippers 8 which grip tube body 2 and impart the motion of motor 38 to said tube body 2. In this case the motor is controlled to impart a clockwise and counter clockwise motion of approximately 30 degrees to the tube body 2. Also seen in this figure is a terminal end 34 of a tube body 2 with projections 36 to secure tube 22 (see FIG. 3) to the tube body 2.

Figure 4:
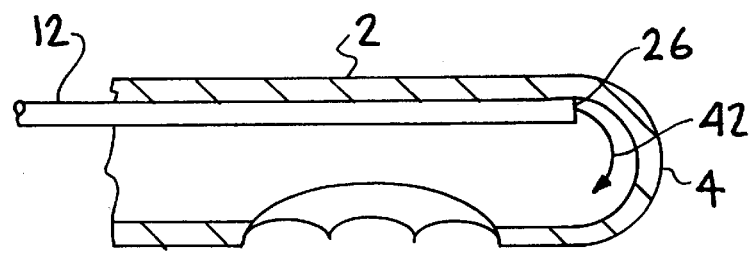
FIG. 4 is a cross-section of the cannula tip.

FIG. 4 is an enlarged cross-sectional view of the distal or tip end of the liposuction cannula. Here is shown how the pressure relief tube 12 terminates near the tip 4 of tube body 2.

Figure 5:
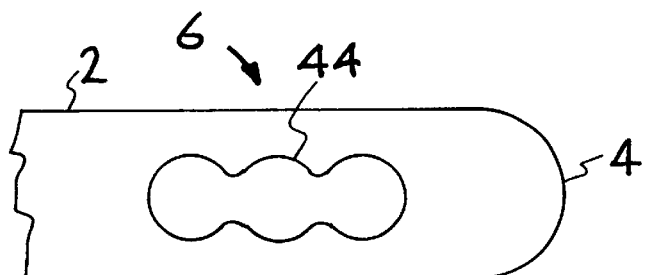
FIG. 5 is a cross-section of the cannula tip turned 90 degrees.

FIG. 5 is also an enlarged view of the tip end 4 of tube body 2 of device 10. In this view the tube 2 has been rotated 90 degrees so that the unique shape of the opening 6 can be shown. The opening or port is herein described as cusped and is given the reference numeral 44.

FIG. 6A and FIG. 6B are both cross-sectional views of the tube body 2 in the area of port 6. FIG. 6A shows the tube body 2 rotated by angle 46, which will be approximately 15 degrees. FIG. 6B shows the tube body 2 rotated in the opposite direction by angle 48, also approximately 15 degrees. This will provide a total reciprocating motion of about 30 degrees to the tube body 2.

In FIG. 7 is shown an alternate method of imparting the oscillating motion to the cannula tube body 2. Here tube body 2 is retained by gripper 8 which is connected to inner housing 64, which is free to oscillate within outer housing 54. Inner housing 64 has a projection or vane 66 which resides within a chamber 68. A shuttle valve 50 alternately applies vacuum from vacuum source 24 to first one side and then the other of vane 66 through ports 58 and 62 respectively. The ports are located in projections 56 and 60 of outer housing 54. The alternating of the vacuum source 24 imparts oscillation motion to tube 2 as shown by arrow 70. FIG. 8A partially illustrates an instrument, generally indicated at 80, which basically includes a cannula shaft 81, an ultrasound source 82, an ultrasonic wire or member 83 which is connected to the source 82, extends through cannula shaft 81 and is fastened at 83' to shaft tip 84. The cannula shaft 81 is provided with a tip opening 85 which may be configured as described above and through which fat indicated at arrows 86 is drawn by a vacuum system through the shaft 81, as indicated by arrow 87. The cannula shaft 81 is connected to a motor, such as descried above, which produces a rotational reciprocating or oscillating motion, as indicated by arrow 88 and as described above. Ultrasonic energy produced by source 82 is transmitted via wire or member 83, as indicated by arrow 89, which produces ultrasonic motion in shaft tip 84.

FIG. 8B shows the tip 84 of the FIG. 8A embodiment being beveled, as indicated at 84', with the wire 83 terminating at the beveled tip 84' as indicated at 83'.

Figure 9:
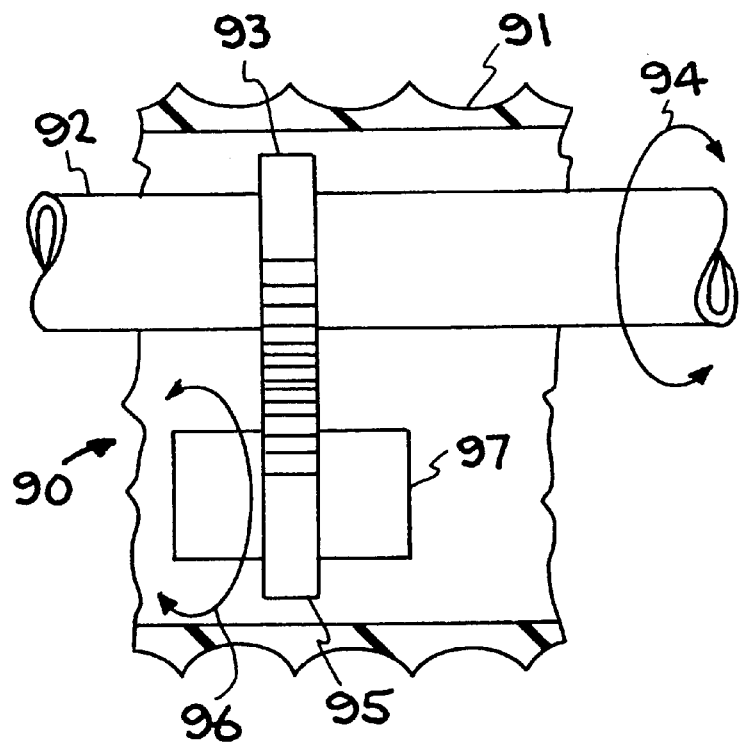
FIG. 9 is a partial cross-section of the handle section of a cannula instrument with a gearing arrangement to enable counter rotational motion of the shaft.

FIG. 9 is a partial cross-section of a handle or handpiece of a cannula instrument which includes a mechanism 90 for cancelling the torque imparted to a handle 91 by the reciprocating motion of the cannula shaft 92. The cannula shaft 92 is connected to a gear segment 93 which turns (rotates) with shaft 91, as indicated by arrow 94. As shaft 92 and gear segment 93 turn (rotate), a connected gear segment 95 is turned (rotated) in the opposite direction, as indicated by arrow 96. A counter weight 97 is secured to gear segment 95 and is of a mass that will cancel the torque imported to the handle 91 by the motion of cannula shaft 92. This will lessen the fatigue of the operator of the cannula instrument.

Figure 10:
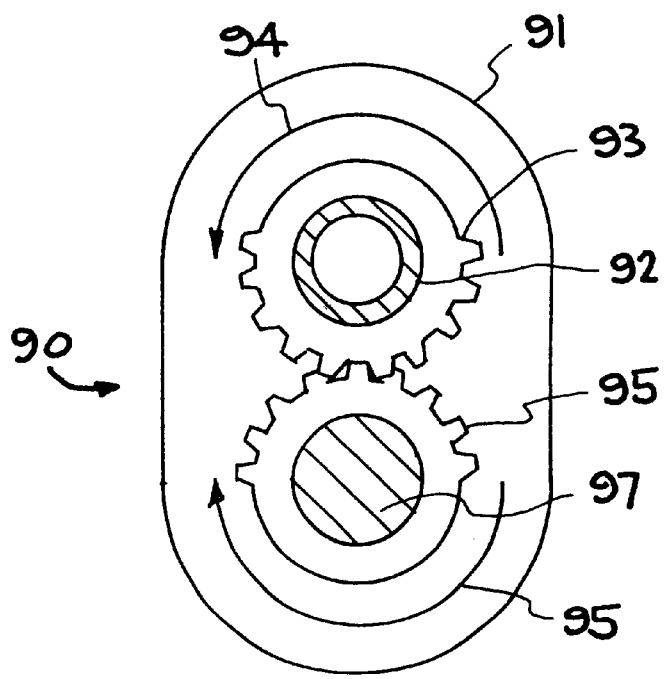
FIG. 10 is a cross-section of the handle of FIG. 9 showing a side view of the gearing arrangement.

FIG. 10 is a cross-section of the FIG. 9 mechanism showing the components of FIG. 9 and how they interact.

It has thus been shown that the present invention provides an improved reciprocating liposuction cannula device which: 1) utilizes a single shaft, 2) provides rectilinear or rotational oscillation single shaft action, 3) utilizes combined vacuum and ultrasonic energy, and 4) uses the extra available vacuum energy for rotational oscillation motion of the single shaft along with the suctioning capacity.

While particular embodiments of the liposuction cannula device have been illustrated and/or described, and particular parameters, etc. have been set forth to exemplify and teach the principles of the invention, such are not intended to be limiting. Modification and changes may become apparent to those skilled in the art, and it is intended that the invention be limited only by the scope of the appended claims.

What is claimed is:

1. A liposuction cannula apparatus, including:
   a single cannula suction shaft,
   means for holding and maneuvering said shaft,
   means for driving said shaft in a rotational oscillation motion, and
   reciprocating means energized by vacuum energy.

2. The apparatus of claim 1, wherein said means for driving said shaft produces energy applied to said shaft which generates a combination of ultrasonic motion from a source and rotational oscillation motion from a source.

3. The apparatus of claim 1, wherein vacuum energy from said source is in the range of about −10 to −40 torr, and wherein about −10 to −15 torr is utilized in said suction means, and wherein vacuum energy in excess of that utilized in said suction means is utilized in said means for driving the rotational oscillation motion of said shaft.

4. In a reciprocating liposuction cannula device, the improvement comprising:
   a single cannula shaft, and
   means utilizing energy from a combination of at least ultrasonic energy and vacuum energy for driving said shaft in a non-rectilinear motion at a distal end thereof.

5. The improvement of claim 4, wherein said single cannula shaft is mounted to a handpiece, said handpiece being operatively connected to said means for driving said shaft.

6. The improvement of claim 4, wherein said shaft has a distal end for aspirating fluid material through said shaft.

7. The improvement of claim 4, wherein one end of said shaft is mounted in a handpiece, and wherein said handpiece includes a swan neck formation.

8. The improvement of claim 4, wherein said shaft is provided with a tube within the cannula shaft for delivering fluid to the distal end of said shaft.

9. The improvement of claim 4, wherein said shaft is hollow, has a distal end selected from the group consisting of curved and beveled configurations, and an opening adjacent said distal end.

10. The improvement of claim 9, wherein said hollow shaft is provided with means for directing fluid to a distal end thereof.

11. The improvement of claim 9, wherein said hollow shaft is provided with means for producing ultrasonic energy at the distal end thereof.

12. The improvement of claim 4, wherein said means for driving said shaft includes an electric motor.

13. A liposuction device, comprising:
   a handpiece,
   a cannula shaft operatively connected to said handpiece,
   a motor located in said handpiece and operatively connected to said cannula shaft for generating non-rectilinear rotational oscillation motion at a distal end of said cannula shaft,
   suction means operatively connected to reciprocate said shaft and for aspirating fluid material through said shaft.

14. The device of claim 13, additional including a swan neck formation interconnecting said handpiece to said cannula shaft.

15. The device of claim 13, additionally including a lumen located within said cannula shaft for delivering a fluid to the distal end of said cannula shaft.

16. The device of claim 13, wherein the fluid delivered by said lumen within said cannula shaft is selected from the group consisting of air at atmospheric pressure, pressurized fluid, and gas.

17. The device of claim 13, wherein said motor is an electric motor.

18. The device of claim 13, wherein said motor is of a type driven by negative pressure.

19. The device of claim 13, wherein said motor is of a type driven by fluid under pressure.

20. The device of claim 13, wherein said cannula shaft is provided at the distal end thereof with a series of scalloped edges or geometric edges.

21. The device of claim 13, additionally including a counter rotating component for canceling rotational torque of the cannula shaft.

22. The device of claim 13, additionally including means for generating concomitant ultrasonic vibration at least in the distal end of the cannula shaft.

23. The device of claim 13, additionally including a member extending through said cannula shaft and attached to an ultrasonic source for generating ultrasonic vibration through the cannula shaft.

24. The device of claim 13, additionally including a counter-rotating gearing arrangement mounted to said motor.

* * * * *